(12) United States Patent
Krekeler

(10) Patent No.: US 10,335,443 B2
(45) Date of Patent: Jul. 2, 2019

(54) ORODISPERSIBLE FILM

(71) Applicant: HEXAL AG, Holzkirchen (DE)

(72) Inventor: Andreas Krekeler, Holzkirchen (DE)

(73) Assignee: HEXAL AG, Holzkirchen (DE)

( * ) Notice: Subject to any disclaimer, the term of this patent is extended or adjusted under 35 U.S.C. 154(b) by 247 days.

(21) Appl. No.: 15/325,899

(22) PCT Filed: Jul. 16, 2015

(86) PCT No.: PCT/EP2015/066332
§ 371 (c)(1),
(2) Date: Jan. 12, 2017

(87) PCT Pub. No.: WO2016/009001
PCT Pub. Date: Jan. 21, 2016

(65) Prior Publication Data
US 2017/0182105 A1    Jun. 29, 2017

(30) Foreign Application Priority Data

Jul. 17, 2014 (EP) ..................... 14177400

(51) Int. Cl.
| | | |
|---|---|---|
| A61K 36/00 | (2006.01) | |
| A61K 36/25 | (2006.01) | |
| A61K 9/00 | (2006.01) | |
| A61K 47/38 | (2006.01) | |

(52) U.S. Cl.
CPC ............. *A61K 36/25* (2013.01); *A61K 9/006* (2013.01); *A61K 47/38* (2013.01)

(58) Field of Classification Search
CPC ..................................... A61K 36/00
USPC ....................................... 424/725
See application file for complete search history.

(56) References Cited

U.S. PATENT DOCUMENTS 5,290,557 A * 3/1994 Mason .................. A01N 43/90
424/410
2013/0216594 A1   8/2013 Krekeler et al.

FOREIGN PATENT DOCUMENTS

| EP | 2732813 A1 | 5/2014 |
|---|---|---|
| JP | 2008063269 A | 3/2008 |
| JP | 2009501751 A | 1/2009 |
| JP | 2009501752 A | 1/2009 |
| JP | 2009530291 A | 8/2009 |
| JP | 2011522883 A | 8/2011 |
| JP | 2013525394 A | 6/2013 |
| JP | 2014074078 A | 4/2014 |
| JP | 2014516061 A | 7/2014 |
| WO | 03011259 A1 | 2/2003 |
| WO | 2004087183 A1 | 10/2004 |
| WO | 2005037298 A1 | 4/2005 |
| WO | 2005037299 A1 | 4/2005 |
| WO | 2007009800 A2 | 1/2007 |
| WO | 2007009801 A2 | 1/2007 |
| WO | 2007149902 A1 | 12/2007 |
| WO | 2010146601 A1 | 12/2010 |

OTHER PUBLICATIONS

Notification of Reasons for Refusal dated Nov. 10, 2017 for corresponding Japanese Application No. 2016-570289, 7 pp.
Office Action of the corresponding Japanese Application No. 2016-570289 dated Jul. 3, 2018, 3 pp.
International Search Report dated Oct. 26, 2015 for corresponding foreign Application No. PCT/EP2015/066332, 5 pp.
International Written Opinion dated Oct. 26, 2015 for corresponding foreign Application No. PCT/EP2015/066332, 5 pp.
Meenu Dahiya et al.; "A review on Mouth Dissolving Films", Current Drug Delivery, vol. 600, Jan. 1, 2009, pp. 469-476.
Denis J.-P. Labarre et al.; "Biomedical and Pharmaceutical Polymers", 2011, Pharmaceutical Press, pp. 27-28.

* cited by examiner

*Primary Examiner* — Michael V Meller
(74) *Attorney, Agent, or Firm* — United IP Counselors, LLC

(57) ABSTRACT

The present invention relates to orodispersible films comprising a plant extract and to film forming suspensions comprising a plant extract. Further, the present invention relates to processes for preparing the orodispersible films and the film forming suspensions.

1 Claim, No Drawings

ORODISPERSIBLE FILM

CROSS-REFERENCE TO RELATED APPLICATIONS

This application is the U.S. National Phase of PCT International Application No. PCT/EP2015/066332, filed on Jul. 16, 2015. That application claims priority to European Patent Application No. 14177400.0, filed Jul. 17, 2014. The contents of both applications are herein incorporated by reference in their entirety.

FIELD OF THE INVENTION

The present invention relates to orodispersible films comprising a plant extract. The present invention further relates to film forming suspensions comprising plant extracts and to processes for preparing the orodispersible films and the film forming suspensions.

BACKGROUND OF THE INVENTION

The oral administration of drugs still represents the most widely used method of administration. Traditional forms of administration are, for example, tablets or capsules, which are generally swallowed. However, this requires that the patient has access to a liquid and is capable of holding e.g. a glass of water, with which he can take the dosage form. To some extent, however, particularly in elderly persons and children who have a narrower esophagus, there is discomfort in swallowing, such that these patients refuse the intake of tablets or capsules, or the intake only happens reluctantly. This, not infrequently, results in poor medication compliance, which has adverse effects for the healing progress and the success of the therapy.

This is particular evident in child patients for which monitoring of the actual medication intake is essential; in such cases the administration of conventional dosage forms such as tablets or capsules is not unproblematic. Due to delayed disintegration, such carriers of active ingredients can easily be removed from the mouth.

To overcome these problems, pharmaceutical dosage forms have been developed, such as for example granules or oral films which can be taken without fluids and which disintegrate rapidly in the oral cavity.

Fast dissolving films are gaining interest as an alternative of fast dissolving tablets. The films are designed to dissolve upon contact with a wet surface, such as the tongue, within a few seconds. This offers the advantage that the consumer can take the product without the need for additional liquid: the salivary fluid in the oral cavity is sufficient to dissolve the film and release the drug. This convenience provides both a marketing advantage and increased patient compliance. Additionally, in many cases, the drug is directly absorbed into systemic circulation, whereby degradation in the gastrointestinal tract and first pass effects can be avoided.

These points make such formulations most popular and acceptable among pediatric and geriatric patients and patients with fear of choking.

Oral films containing pharmaceutical and non-pharmaceutical active ingredients, and processes for their preparation are described, for example, in WO 2007/009800, WO 2007/009801 and WO 03/011259.

Herbal medicines (phyto-pharmaca) enjoy considerable importance in the treatment of patients and self-medication (phyto-therapy). Phyto-pharmaca are defined, according to the German law regulating the use of drugs, as being substances derived by plants or parts thereof, whether processed or not. Plant extracts or phyto-extracts are concentrated pharmaceutical preparations of plants obtained by removing active constituents with a suitable solvent, which is evaporated. The residue is then adjusted to the prescribed standard. The plant extract can be then prepared in oil form, concentrated solution form, dry form etc.

Phyto-pharmaca are mixtures of several substances and are therefore fundamentally different from drugs based on an active pharmaceutical ingredient (API) in the pure form. The medical activity of the phyto-pharmaca derives from the mixture of substances contained in the plant extract.

Plant extracts are used as such rather than identifying and isolating the API. This offers an advantage especially when the active constituent is not known, but the mixture has proven clinical efficacy. Moreover, even if one or more active ingredients are known, further substances may be responsible for an optimal effect.

When the active agent is known, standardized extracts are prepared to contain the same amount of the active ingredient. For extracts whose main active constituents are unknown, the entire process from the cultivation to the preparation of the extract is standardized.

Phyto-pharmaca show an increased tolerance and compliance with respect to chemically synthesized dugs. Because of their natural source, phyto-pharmaca have the advantage of being well accepted by the public. One consequence is the readiness of the patient to take the medicines regularly, which is important for the success of the therapy.

Amongst the plant extracts, there is a long tradition of using the dry extract of *Hedera helix* (common ivy) leaves in traditional and contemporary alternative medicine. Many biological and pharmacological studies have been aimed at evaluating the effects of ivy. The results suggest that *Hedera helix* extract possesses bronchodilatatory and antispasmodic activity. The effect is thought to be due to the two main substances extracted from the plant: α-hederin and hederacoside C.

Extracts from ivy leaves are currently employed successfully in particular for the therapy of respiratory disorders, because the extract shows spasmolytic, expectorant and antiobstructive effects.

Processes for preparing extracts from plant materials are disclosed for example in WO2004/087183, WO2005/037298 and WO2005/037299. These publications disclose ivy extracts which have a specifically adjusted content of [alpha]-hederin and/or hederacoside C, and processes with which such extracts can be provided.

Plant extracts are generally in the dry form, in the form of oils, concentrated solutions or concentrated hydro-alcoholic solutions that are not suitable to be administered especially to children. There is therefore the need to provide formulations of plant extracts that meet the compliance requirements of the patients, in particular of children.

SUMMARY OF THE INVENTION

The above mentioned problems are solved by the orodispersible films of the invention. The orodispersible films of the invention comprise a plant extract and a film forming polymer having a selected number average molecular weight (Mn).

Hence, in a first aspect, the present invention is directed to an orodispersible film comprising:

a) a plant extract; and b) a film forming polymer wherein the film forming polymer has a number average molecular weight (Mn) ranging from 15000 Da (g/mol) to 30000 Da (g/mol).

In a second aspect, the present invention is directed to a film forming suspension comprising:
a) a plant extract;
b) a film forming polymer wherein the film forming polymer has a number average molecular weight (Mn) ranging from 15000 Da (g/mol) to 30000 Da (g/mol); and
c) a solvent or a mixture of solvents.

In a third aspect the present invention is directed to an orodispersible film obtainable by evaporating the solvent of a film forming suspension wherein
the film forming suspension has a viscosity ranging from 1000 to 5000 mPa·s, preferably ranging from 2000 to 4000 mPa·s, even more preferably ranging from 2500 to 3500 mPa·s and
the film forming suspension comprises a plant extract and a film forming polymer.

In a fourth aspect, the present invention is directed to an orodispersible film for use as a medicament.

In a fifth aspect, the present invention is directed to an orodispersible film for use in preventing or treating respiratory diseases.

In a sixth aspect, the present invention is directed to method for preparing the orodispersible film.

In a seventh aspect, the present invention is directed to a method for preparing the film forming suspension of the invention. The method comprises mixing the plant extract with a film forming polymer of the invention In an eight aspect, the present invention is directed to a packaging comprising the orodispersible film according to the present invention.

DETAILED DESCRIPTION OF THE INVENTION

The present invention relates to an orodispersible film comprising a plant extract and a film forming polymer having a selected number average molecular weight (Mn) and optionally a selected weight average molecular weight (Mw). The orodispersible film of the invention may, preferably, further comprise microcrystalline cellulose.

It has been seen that orodispersible films comprising a plant extract are cumbersome to make due to the nature of the plant extracts. Plant extracts are generally in an oil form, concentrated solution or dry form. They are composed of several chemical compounds which are not in theft pure form. Hence, plant extracts and the active ingredients are not in the form of crystalline solids compounds, nor they are in the form of nanoparticles.

With the ambition to prepare orodispersible films of plant extracts, the present inventors have found that commonly used film forming polymers are not suitable for preparing orodispersible films comprising a plant extract. For example, the commonly used film forming polymer Methocel E5LV leads to brittle films with no elasticity and insufficient mechanical strength, while the use of the film forming polymer Metolose 60 SH-50 leads to sticky films which cannot be removed from the process liner or the primary packaging and show an insufficient disintegration time.

Surprisingly, the present inventors have found that plant extracts may be optimally formulated in orodispersible films by selecting film forming polymers with a medium molecular weight. In particular, the plant extracts may be formulated by using a film forming polymer with a selected number average molecular weight (Mn) and, preferably, by a film forming polymer with both a selected number average molecular weight (Mn) and a selected weight average molecular weight (Mw). Best results are obtained when hydroxypropyl methyl cellulose (HPMC) is used as film forming polymer having the selected number average molecular weight (Mn) and, preferably, both the selected number average molecular weight (Mn) and the selected weight average molecular weight (Mw).

Hence, the present invention is directed to an orodispersible film comprising a plant extract and a film forming polymer having a Mn ranging from 15000 Da (g/mol) to 30000 Da (g/mol). Preferably, the film forming polymer has a Mn ranging from 20000 Da (g/mol) to 30000 Da (g/mol); more preferably, the film forming polymer has a Mn ranging from 23000 Da (g/mol) to 27000 Da (g/mol).

The film forming polymer of the invention preferably has a weight average molecular weight (Mw) ranging from 32000 Da (g/mol) to 80000 Da (g/mol). More preferably, the film forming polymer has a Mw ranging from 40000 Da (g/mol) to 80000 Da (g/mol). Even more preferably, the film forming polymer has a Mw ranging from 50000 Da (g/mol) to 70000 Da (g/mol). Most preferably, the film forming polymer has a Mn ranging from 23000 Da (g/mol) to 27000 Da (g/mol) and a Mw ranging from 50000 Da (g/mol) to 70000 Da (g/mol).

It has been found that the film forming polymers according to the invention confer to the film forming suspension an optimal viscosity for the preparation of orodispersible films comprising plant extracts.

The number average molecular weight "Mn" and the weight average molecular weight "Mw" of the film forming polymers is determined according to the literature source: C.M. Keary, Carbohydrate Polymers 45 (2001) 293-303.

In particular, the following setup and settings are employed:

| | |
|---|---|
| Measurement method: | SEC (Size Exclusion Chromatography) |
| Sample concentration | 2 mg/ml |
| Eluant: | NaCl 0.05M |
| Column: | Two columns in series: 1. TosoHaas, TSK GMPW XL, 7.8 mm × 30 cm, 2. TSK column guard PW XL |
| Column temperature: | 45° C. |
| Detector: | combined LS-DP-RI detector (laser light scattering/viscometer detector/laser refractometer) |
| Calibration standard: | Pullulan (MW = 100 000) |

First Aspect: Orodispersible Films

In a first aspect, the present invention provides an orodispersible film comprising:
a) a plant extract; and
b) a film forming polymer wherein the film forming polymer has a number average molecular weight (Mn) ranging from 15000 Da (g/mol) to 30000 Da (g/mol).

Preferably, the film forming polymer according to the invention has a Mn ranging from 20000 Da (g/mol) to 30000 Da (g/mol), more preferably the film forming polymer has a Mn ranging from 23000 Da (g/mol) to 27000 Da (g/mol), even more preferably, the film forming polymer has a Mn ranging from 25000 Da (g/mol) to 26000 Da (g/mol).

The film forming film has preferably a weight average molecular weight (Mw) ranging from 32000 Da (g/mol) to 80000 Da (g/mol); preferably the film forming polymer has a Mw ranging from 40000 Da (g/mol) to 80000 Da (g/mol); more preferably the film forming polymer has a Mw ranging from 50000 Da (g/mol) to 70000 Da (g/mol); even more preferably the film forming polymer has a Mw ranging from 55000 Da (g/mol) to 65000 Da (g/mol).

It has been seen that when the Mn and Mw values exceed the Mn value of 30000 Da (g/mol) and the Mw value of 80000 Da (g/mol), respectively, the orodispersible film has poor pull-off properties and it is not removable from the process liner. On the contrary, if the Mn and optionally the Mw values are lower than the Mn value of 15000 Da (g/mol) and the Mw value of 32000 Da (g/mol), the resulting orodispersible film is brittle, lacks elasticity and mechanical strength.

It has been seen that film forming polymers that can be used are cellulose, cellulose ester (such as cellulose acetate), cellulose ether (such as hydroxypropyl methyl cellulose (HPMC), hydroxyethyl methyl cellulose, sodium carboxymethyl cellulose, hydroxypropyl cellulose, hydroxyethyl cellulose, ethyl cellulose, methyl cellulose) polyethylene oxide, polyvinyl pyrrolidone (e.g. PVP K-90), polyvinyl alcohol, pullulan, starch, modified starch, gelatin, pectin, alginate, and combinations thereof, preferably hydroxypropyl methyl cellulose (HPMC such as Methocel E15LV). These polymers exist and are commercially available in a wide range of Mn and Mw values. The polymers according to the invention have the Mn and optionally the Mw values as disclosed above in the context of the invention.

For example, the commercially available HPMC "Methocel E15LV" has a Mn=25000 Da (g/mol) and a Mw=60000 Da (g/mol) and is an excellent film forming polymer for preparing the orodispersible film comprising the plant extract according to the invention. HPMC having a Mn=25000 Da (g/mol) and a Mw=60000 Da (g/mol) is the preferred film forming polymer according to the present invention.

Optimally, the percentage weight (based on the dry weight of the orodispersible film) of the film forming polymer in the orodispersible film ranges from 5 to 40% wt., preferably ranges from 10 to 30% wt., more preferably ranges from 15 to 25% wt.; even more preferably from 19 to 21% wt.

It has been seen that the pull-off properties of the orodispersible film of the invention may be further optimized by the addition of microcrystalline cellulose (MCC). Orodispersible films comprising plant extracts may sometimes show excessive stickiness resulting in that the orodispersible films cannot be processed. This drawback is particular evident when dry plant extracts are used. In contrast hereto, the orodispersible films of the invention further comprising MCC result in orodispersible films with high mechanical strength, a fast disintegration time, non-sticky properties and good processability. The present inventors have found that an optimal weight ratio of the film forming polymer related to MCC ranges from 0.5:1 to 3.5:1, preferably from 1:1 to 3:1, more preferably from 1.5:1 to 2.5:1, even more preferably the ratio is 1.5:1 to 2:1.

Preferably, the film forming polymers "HPMC" according to the invention and MCC are used in the above indicated ratios.

According to the present invention, the orodispersible film further, preferably, comprises a plasticizer. The plasticizer may serve to further reduce the brittleness of the orodispersible film and to increase its flexibility. Any plasticizer suitable for the purpose of preparing an orodispersible film can be used. In a preferred embodiment, the plasticizer may be selected from glycerol, propylene glycol, dibutyl sebacate, triacetin, triethyl citrate, isopropyl myristate and combinations thereof. The use of propylene glycol or glycerol is particularly preferred. Glycerol is the most preferred plasticizer.

The orodispersible film of the invention optionally comprises from 2.5 to 20% wt. of plasticizer, preferably the orodispersible film comprises from 5 to 20% wt. of plasticizer, more preferably the orodispersible film comprises from 7.5 to 15% wt. of plasticizer, even more preferably the orodispersible film comprises from 10 to 15% wt. of plasticizer.

The present inventors have found that the plasticizer together with MCC contribute to reduce the stickiness and to improve the removability of the orodispersible film from the process liner. The present inventors have found that an optimal weight ratio of the microcrystalline cellulose relative to the plasticizer is in the range from 0.5:1 to 2:1, preferably of from 0.8:1 to 1.2:1, even more preferably is 1:1.

The orodispersible film according to the invention comprises a plant extract. The term plant extract as used herein means "concentrated pharmaceutical preparation of plants or part of plants obtained by removing active constituents with a suitable solvent, which is evaporated. The residue is then adjusted to the prescribed standard." The plant extract can be then prepared in the oil form, concentrated solution form, dry form etc. Dry extracts are extracts of plant material which are evaporated into a dry mass.

The plant extracts to be formulated according to the present invention are in the form of a concentrated solution or a dry extract such as in the form of powder. Preferably, they are in the form of dry extracts. Plant extracts according to the present invention are phyto-pharmaca, i.e. they have one or more therapeutic or prophylactic indications. Plant extracts having therapeutic or prophylactic indications are generally known.

Preferably, the plant extracts of the invention are useful in the treatment of respiratory diseases. Respiratory diseases according to the invention are for example respiratory diseases wherein relaxation of smooth muscle is desired. Respiratory diseases according to the invention are for example common cold, influenza, pneumonia, tracheitis, bronchitis, chronic bronchitis, pulmonary emphysema, asthma, chronic or acute bronchoconstriction, stridulus infant syndrome, chronic obstructive pulmonary disease, bronchial adenoma, solitary pulmonary nodule, pulmonary tuberculosis, pyothorax, pulmonary abscess and pulmonary histiocytosis, etc.

Plant extracts according to the present invention useful in the treatment of respiratory disease are for example ivy extracts, preferably *hedera helix* leaf dry extract, coptidis rhizoma extract, *primula veris* extract, *primula elatior* extract, *thymus vulgaris* extract or mixtures thereof.

Ivy extracts can be selected from a variety of ivy such as *hedera helix* extract, *hedera algeriensis* extract, *hedera azorica* extract, *hedera canariensis* extract, *hedera colchica* extract, *hedera hibernica* extract, *hedera maderensis* extract, *hedera nepalensis* extract, *hedera pastuchowii* extract, *hedera rhombea* extract. *Hedera helix* extract is the preferred extract according to the invention.

The content of the plant extract in the orodispersible film of the invention ranges from 25 to 50% wt., preferably from 30% to 45% wt., even more preferably from 35% to 40% wt. related to the dry weight of the suspension or orodispersible film.

The orodispersible film according to the invention preferably comprises:
1) from 25 to 50% wt. of plant extract, for example a *hedera helix* leaf dry extract;

2) from 10 to 30% wt. of film forming polymer of the invention, preferably of hydroxypropyl methyl cellulose (HPMC);
3) from 2.5 to 20% wt. of microcrystalline cellulose;
4) from 2.5 to 20% wt. of plasticizer, preferably glycerol; and
5) optionally, 3 to 10% wt. of a diluent, preferably maltodextrin;

each % wt. based on the dry weight of the orodispersible film.

The orodispersible film according to the invention more preferably comprises
1) from 30% to 45% wt. of plant extract, for example a *hedera helix* leaf dry extract;
2) from 15% to 25% wt. of film forming polymer of the invention, preferably of hydroxypropyl methyl cellulose (HPMC);
3) from 7.5% to 15% wt. of microcrystalline cellulose;
4) from 7.5% to 15% wt. of plasticizer, preferably glycerol; and
5) optionally, 5% to 8% wt. of a diluent, preferably maltodextrin;

each % wt. based on the dry weight of the orodispersible film.

The orodispersible film according to the invention even more preferably comprises:
1) from 35% to 40% wt. of plant extract, for example a *hedera helix* leaf dry extract;
2) from 17% to 23% wt. of film forming polymer of the invention, preferably of hydroxypropyl methyl cellulose (HPMC);
3) from 8.5% to 12% wt. of microcrystalline cellulose;
4) from 8.5% to 12% wt. of plasticizer, preferably glycerol; and
5) optionally, from 5% to 6.5% wt. of a diluent, preferably maltodextrin, Additionally, the orodispersible film of the invention may comprises at least one excipient selected from a wetting agent, a flavoring, a taste masker, a preservative, a sweetener, a coloring agent. The quantities of these additional excipients are adjusted accordingly based on the above weight percentage to achieve the 100% wt. total of the dry weight of the orodispersible film.

One of the preferred orodispersible films of the invention comprises
a) from 35 to 40% wt. (e.g. 37.5% wt.) *hedera helix* leaf dry extract;
b) from 19 to 21% wt. (e.g. 20% wt.) HPMC having the Mw and the Mn values according to the invention, preferably having Mn=25000 Da (g/mol) and Mw=60000 Da (g/mol);
c) from 10 to 15% wt. (e.g. 11% wt.) MCC;
d) from 10 to 15% wt. (e.g. 12.5% wt.) glycerol;
e) from 5 to 7.5% wt. (e.g. 5.5% wt.) maltodextrin,
based on the dry weight of the orodispersible film. It may further comprises titanium oxide, sucralose and a flavor.

One of the preferred orodispersible films of the invention comprises
a) 37.5% wt. *hedera helix* leaf dry extract;
b) 20% wt. HPMC having the Mw and the Mn values according to the invention, preferably having Mn=25000 Da (g/mol) and Mw=60000 Da (g/mol);
c) 11% wt. MCC;
d) 12.5% wt. glycerol; and
e) 5.5% wt. maltodextrin,
based on the dry weight of the orodispersible film. It may further comprise titanium oxide, sucralose and a flavor.

Typically the orodispersible film has a weight that ranges from 70 to 100 g/m$^2$, preferably it is 80 g/m$^2$.

Disintegration Time

The orodispersible film of the invention rapidly disintegrates in the oral cavity of a patient. The disintegration time is preferably less than 100 seconds, more preferably less than 60 seconds, even more preferably less than 20 seconds. The disintegration time is determined as described below in the context of the Examples.

It has been surprisingly found by the present inventors that the film forming polymer having the medium molecular weight Mn and Mw of the invention as disclosed above improves the disintegration of the film in the oral cavity by reducing the disintegration time. It is believed that the optimal viscosity conferred by the film forming polymer, having the above Mn and Mw values of the invention, to the film forming solution and to the orodispersible film is one of the reasons for the optimal disintegration time achieved by the orodispersible film of the invention.

Thickness

The orodispersible film of the invention has a dry film thicknesses ranging from 50 μm to 500 μm, preferably from 100 μm to 200 μm, more preferably from 140 μm to 180 μm. A dry film thickness within and including the mentioned limits ensures rapid disintegration of the film within the oral cavity. This ensures that the plant extract is completely absorbed by the patient. Additionally, a dry film thickness within and including the mentioned limits ensures a pleasant mouth feeling which is important for patient compliance. Also films with lower or higher layer thicknesses can be provided for specific requirements, which are encompassed by the invention as well.

It has been observed that the use of the film forming polymer of the invention allows having a thinner orodispersible film, yet with a good mechanical strength. One problem in film production is the tendency of the film to be damaged during pull-off. Thicker films are less affected by this problem. However, thick films have a longer disintegration time and are generally less favorable in relation to patient compliance. The present inventors have found that thicker films prepared with a film forming polymer having a Mn above 30000 Da (g/mol) result in sticky films. Instead, the present film forming polymer alone or together with MCC, preferably when used in the above mentioned ratios of the film forming polymer relative to MCC, even more preferably when used in the above mentioned ratios of the film forming polymer relative to the plasticizer, solves the problem of stickiness and provides an optimal balance between film thickness requirements and pull-off integrity.

Additional Excipients

The orodispersible film of the invention may further comprise one or more excipients selected from a wetting agent, a flavoring, a taste masker, a preservative, a sweetener, a coloring agent and a filler. These are disclosed in details in the section below: "Additional pharmaceutical acceptable excipients".

Second Aspect: Film Forming Suspension

In a second aspect, the present invention is directed to a film forming suspension comprising:
a) a plant extract;
b) a film forming polymer wherein the film forming polymer has a number average molecular weight (Mn) ranging from 15000 Da (g/mol) to 30000 Da (g/mol); and
c) a solvent or a mixture of solvents.

The film forming suspensions disclosed herein have the same components of the orodispersible film disclosed above in the first aspect. This is because an orodispersible film of the invention can be prepared starting from a film forming suspension of the second aspect of the invention and contains the same components. The difference between the orodispersible film and the film forming suspension is thus the solvent.

Plant Extract

The plant extracts are preferably as disclosed above in the first aspect of the invention and its embodiments.

The content of the plant extract in the film forming suspension of the invention is preferably from 25 to 50% wt., preferably from 30% to 45% wt., even more preferably from 35% to 40% wt. related to the dry weight of the suspension.

Solvents

Solvents suitable according to the invention are water, ($C_1$-$C_5$) alcohol or acetone. Water may be present as the sole solvent or may be present in a mixture with one or more solvents selected from a ($C_1$-$C_5$)-alcohol and acetone. The mixture of solvents in the present context may be referred to as the "solvent system".

Preferably, a solvent system is used to prepare the film forming suspension of the invention. Preferred solvents (in addition to water) of the solvent system are ethanol or isopropanol; hence, the solvent system is preferably a mixture of 1) water and ethanol or 2) water and isopropanol. Even more preferably, the solvent system is a mixture of water and ethanol.

The amount of solvent other than water in the solvent system is from 0% (v/v) to 65% (v/v), preferably from 20% (v/v) to 40% (v/v), even more preferably from 25% (v/v) to 35% (v/v) of the solvent system. Hence, in the preferred solvent system of water/ethanol, the amount of ethanol is from 0% (v/v) to 65% (v/v), preferably from 20% (v/v) to 40% (v/v), even more preferably from 25% (v/v) to 35% (v/v).

Acetone can also be present in the solvent system. In this case, acetone preferably does not exceed 5% (v/v) of the solvent system.

The percentage amounts refer to the solvent system.

Viscosity

The film forming suspension of the invention has preferably a viscosity (dynamic viscosity) at 25° C. of from 1000 mPa·s to 5000 mPa·s, more preferably 2000 mPa·s s to 4000 mPa·s, even more preferably 2500 mPa·s to 3500 mPa·s (measured with a cone-plate viscometer at a shear rate of 1/100 sec according to Ph. Eur. 7.0 chapter 2.2.10). A high viscosity of the film forming suspension is preferable in general to obtain a stable suspension free from sedimentation problems. On the other hand, in conjunction with the plant extracts of the invention, a highly viscous suspension will result in a sticky film. The use of the film forming polymer having the preferred Mn and optionally also the Mw values of the invention allows suspensions with an optimal viscosity. Since suspensions with lower viscosity can be advantageously used, the above mentioned problems connected with stickiness are avoided by the film forming suspension of the invention.

Additional Excipients

The film forming suspension of the invention may further comprise one or more components selected from a wetting agent, a flavoring, a taste masker, a preservative, a sweetener, a coloring agent and a filler. These are disclosed in details in the below section "Additional pharmaceutical acceptable excipients".

Composition of Film Forming Suspension

A film forming suspension according to the invention preferably comprises
1) from 25 to 50% wt. of plant extract, for example a *hedera helix* leaf dry extract;
2) from 10 to 30% wt. of film forming polymer of the invention, preferably of hydroxypropyl methyl cellulose (HPMC);
3) from 2.5 to 20% wt. of microcrystalline cellulose;
4) from 2.5 to 20% wt. of a plasticizer, preferably glycerol;
5) optionally from 3 to 10% wt. of a diluent, preferably maltodextrin; and
6) a solvent or a mixture of solvents as disclosed above, preferably a mixture of water and ethanol,
wherein the % wt. are based on the dry weight of the film forming suspension.

The film forming suspension according to the invention more preferably comprises
1) from 30 to 45% wt. of plant extract, for example *hedera helix* leaf dry extract;
2) from 15 to 25% wt. of film forming polymer of the invention, preferably of hydroxypropyl methyl cellulose (HPMC);
3) from 7.5 to 15% wt. of microcrystalline cellulose;
4) from 7.5 to 15% wt. of plasticizer, preferably glycerol;
5) from 5 to 8% wt. of maltodextrin; and
6) a solvent or a mixture of solvents as disclosed above, preferably a mixture of water and ethanol,
wherein the % wt. are based on the dry weight of the film forming suspension.

The film forming suspension according to the invention even more preferably comprises
1) from 35 to 40% wt. of plant extract, for example a *hedera helix* leaf dry extract;
2) from 17 to 23% wt. of film forming polymer of the invention, preferably of hydroxypropyl methyl cellulose (HPMC);
3) from 8.5 to 12% wt. of microcrystalline cellulose;
4) from 8.5 to 12% wt. of plasticizer, preferably of glycerol;
5) optionally, from 5 to 6.5% wt. of diluent, preferably maltodextrin; and
6) a solvent or a mixture of solvents as disclosed above, preferably a mixture of water and ethanol,
based on the dry weight of the film forming suspension.

Additionally, the film forming suspension of the invention may comprise at least one additional excipient selected from a wetting agent, a flavoring, a taste masker, a preservative, a sweetener, a coloring agent. The quantity of these additional excipients is adjusted accordingly based on the above weight percentage.

The percentage amounts refer to the dry weight of the film forming suspension. Additionally, the suspension comprises water or a solvent system. Preferred solvent systems are a water/ethanol solvent system and a water/isopropanol solvent system; even more preferred is the water/ethanol solvent system. Preferably, the amount of solvent other than water in the solvent system is from 0% (v/v) to 65% (v/v), preferably from 20% (v/v) to 40% (v/v), even more preferably from 25% (v/v) to 35% (v/v) of the solvent system. Hence in the preferred solvent system of water/ethanol, the amount of ethanol is from 0% (v/v) to 65% (v/v), preferably from 20% (v/v) to 40% (v/v), even more preferably from 25% (v/v) to 35% (v/v). The percentage amounts refer to the solvent system.

One of the preferred film forming suspensions of the invention comprises:
a) from 35 to 40% wt. (e.g. 37.5% wt.) *hedera helix* leaf dry extract;
b) from 19 to 21% wt. (e.g. 20% wt.) HPMC having the Mn and the Mw values according to the invention, preferably having Mn=25000 Da (g/mol) and Mw=60000 Da (g/mol);
c) from 10 to 15% wt. (e.g. 11% wt.) MCC;
d) from 10 to 15% wt. (e.g. 12.5% wt.) glycerol;
e) from 5 to 7.5% wt. (e.g. 5.5% wt.) maltodextrin;
f) water and
g) ethanol.

The percentage relates to the dry weight of the orodispersible film (water and ethanol are not counted in the weight percentage). It may further comprise one or more of titanium oxide, sucralose and a flavor.

One of the preferred film forming suspensions of the invention comprises:
a) 37.5% wt. *hedera helix* leaf dry extract;
b) 20% wt. HPMC having the Mn and the Mw values according to the invention, preferably having Mn=25000 Da (g/mol) and Mw=60000 Da (g/mol);
c) 11% wt. MCC;
d) 12.5% wt. glycerol;
e) 5.5% wt. maltodextrin;
f) water and
g) ethanol.

The percentage relates to the dry weight of the orodispersible film (water and ethanol are not counted in the weight percentage). It may further comprise one or more of titanium oxide, sucralose and a flavor.

Third Aspect: Orodispersible Film

In a third aspect, the present invention is directed to an orodispersible film obtainable by evaporating the solvent of a film forming suspension wherein
the film forming suspension has a viscosity ranging from 1000 to 5000 mPa·s, preferably ranging from 2000 to 4000 mPa·s, more preferably from 2500 to 3500 mPa·s, and wherein
the film forming suspension comprises a plant extract and a film forming polymer.

Preferably, the film forming suspension used to prepare the orodispersible film comprising a plant extract has a viscosity (dynamic viscosity) at 25° C. of from 1000 mPa·s to 5000 mPa·s, more preferably 2000 mPa·s to 4000 mPa·s, even more preferably 2500 mPa·s to 3500 mPa·s (measured with a cone-plate viscometer at a shear rate of 1/100 sec according to Ph. Eur. 7.0 chapter 2.2.10). A high viscosity of the film forming suspension is preferable in general to obtain a stable suspension, free from sedimentation problems. On the other hand, a highly viscous suspension will result in a non-homogeneous sticky film. It has been seen by the present inventors that a film forming suspension having the above viscosity provides an optimal balance for obtaining an orodispersible film comprising a plant extract with excellent pull-off properties and disintegration time.

The orodispersible films according to the third aspect are prepared for example using a film forming suspension as disclosed in the second aspect of the invention and embodiments thereof according to the general and known processes for preparing orodispersible films from a film forming suspension. Hence, for example the orodispersible films of the invention are obtainable from film forming suspensions according to the second aspect of the invention and its embodiments in a process that comprises drying the film forming suspension.

Any film forming polymer suitable for providing the desired viscosity can be used to produce the orodispersible film according to the third aspect of the invention. Film forming polymers that can be used according to the third aspect of the invention are cellulose, cellulose ester (such as cellulose acetate), cellulose ether (such as hydroxypropyl methyl cellulose (HPMC), hydroxyethyl methyl cellulose, sodium carboxymethyl cellulose, hydroxypropyl cellulose, hydroxyethyl cellulose, ethyl cellulose, methyl cellulose) polyethylene oxide, polyvinyl pyrrolidone (e.g. PVP K-90), polyvinyl alcohol, pullulan, starch, modified starch, gelatin, pectin, alginate and combinations thereof, preferably hydroxypropyl methyl cellulose (HPMC such as Methocel E15LV).

Fourth Aspect: Medicaments

In a fourth aspect, the present invention is directed to the orodispersible film of the invention as defined in the first aspect and its embodiments and in the third aspect and its embodiments, for use as a medicament.

Fifth Aspect: Medical Uses

In a fifth aspect, the present invention is directed to an orodispersible film of the first and the third aspects for use in preventing or treating respiratory diseases.

Respiratory diseases according to the invention are for example respiratory diseases wherein relaxation of smooth muscle is desired.

Respiratory diseases are for example common cold, influenza, pneumonia, tracheitis, bronchitis, chronic bronchitis, pulmonary emphysema, asthma, chronic or acute bronchoconstriction, stridulus infant syndrome, chronic obstructive pulmonary disease, bronchial adenoma, solitary pulmonary nodule, pulmonary tuberculosis, pyothorax, pulmonary abscess and pulmonary histiocytosis.

Sixth Aspect: Method for Preparing the Orodispersible Film

In a sixth aspect, the present invention provides a method for preparing an orodispersible film comprising:
a) preparing a film forming suspension as defined above in the second aspect of the invention and in its embodiments; and
b) drying the suspension to form the orodispersible film.

In general, the suspension is homogeneously spread out on a foil (carrier liner) and dried. A second foil (backing foil) can be laminated on top to protect the film, if desired. The foil or foils can be removed afterwards.

Preferably, the drying of the film is done by application of heat. The application of heat can for example be done by a hot air blower. There is of course also the possibility that the film is dried in an oven, on a heated surface or a comparable drying device. The film is preferably dried for 15 to 30 minutes, more preferably for 15 to 20 minutes. The drying temperature may preferably range from 40 to 70° C.

After drying the thus formed film can be cut into the final form representing the single dosage unit, for example into a round, rounded, oval, elliptical, triangular, rectangular, square or polygonal shape. Preferably, the cut film has a size of 1 cm² to 8 cm².

Seventh Aspect: Method for Preparing the Film Forming Suspension

In a seventh aspect, the present invention is directed to a method for preparing the film forming suspension as defined in the second aspect of the invention and its embodiments.

The method comprises mixing (a) the plant extract, (b) water or the mixture of water and a solvent selected from a $(C_1$-$C_5)$alcohol, acetone and mixtures thereof, and (c) the film forming polymer of the invention. The plant extract can be added to the water or the solvent system already containing the film forming polymer of the invention. Alternatively, the film forming polymer of the invention can be added after the plant extract was added to the water or the solvent system. In a further alternative, the plant extract and the film forming polymer can be added to the water or the solvent system simultaneously.

Further substance(s) can be added before, after or simultaneously with the plant extract to the solvent or solvent mixture of the suspension. Additional film forming agents, flavorings, sweeteners and/or plasticizers can be dissolved or dispersed, for example prior to the addition of the plant extract, in the solvent or solvent mixture. The mixture thus obtained can then be used as a solvent for the suspension. Of course, further substances may be added to the suspension later, i.e. for example, after the addition of the plant extract.

Eight Aspect: Packages

In an eight aspect, the present invention is directed to a package comprising the orodispersible film of the invention as defined in the first aspect and its embodiments and in the third aspect and its embodiments. The packaging materials used for oral films are, for example, sachets made from flexible multilayer foils which preferably may have an aluminum barrier layer and a heat sealer layer.

Additional Pharmaceutical Acceptable Excipients

The orodispersible film of the invention and the film forming suspension of the invention may further comprise one or more additional components selected from a wetting agent, a flavoring, a taste masker, a preservative, a sweetener, a coloring agent and a filler.

a) Wetting Agents

A wetting agent may be present in the orodispersible film and in the film forming suspension of the invention. The wetting agents are useful to retain water in the dosage form. A certain amount of water remaining in the film (0.5 to 10% wt., preferably 1 to 8% wt.) is preferable in view of the elasticity, which facilitates the processing of the product and the handling by the patient. Any wetting agent suitable for the purpose of retaining water in the film is contemplated by the present invention. Preferred wetting agents include sugar alcohols, for example sorbitol, and xylitol. The percentage amount of the wetting agent, when present, ranges from 0.5 to 10% wt., preferably 5 to 10% wt. The weight percentages refer to the dry weight of the film or of the suspension.

b) Taste Masking Agents, Flavoring Agents and Sweeteners

Taste masking may be advantageous for plant extracts with a bitter or otherwise unpleasant taste. A flavoring agent may be optionally a further component of the orodispersible film and of the suspension of the invention. Normally, liquid flavors are used, although amounts of flavors may be lost during drying. When a flavor is employed, the proportion in the orodispersible film or in the film forming suspension of the invention is from 0.1 to 10% wt., preferably from 0.5 to 7.5% wt., related to the dry weight of the composition. Peppermint oil, peppermint flavor, menthol, and/or levomenthol are flavors according to the invention. Alternatively or additionally, flavors with sour fresh taste, especially raspberry flavor, grapefruit flavor, lemon and/or orange flavor can be present. The taste of the orodispersible film and the taste sensation occurring after ingestion can thus be made more comfortable for the patient. Further to the aforementioned flavoring agents or combinations of these, the flavoring agent can also be selected from flavoring agents with sweet, nutty taste, in particular from those flavoring agents that produce a nut flavor, a chocolate flavor, a cinnamon or spice flavor or the like. Naturally, there is also the possibility to use a mixture of the aforesaid with the flavoring agents as previously described. Besides the mentioned flavoring agents, any other suitable flavoring agents can be used to determine or define the flavor of respective compositions to thereby increase patient's compliance.

Further systems may be used as taste receptor competitors (e.g. sodium chloride) or bitter masking substances. Ion exchange resins (e.g. Amberlite types) may be also used.

Additionally or alternatively, a sweetener can be used. The sweetener may support taste masking and enhance acceptability of the film. Sweeteners can be selected from monosaccharides, disaccharides, polysaccharides, sucralose, neotame, alitame, cyclamate, sorbitol, xylitol, saccharin, aspartame, and mixtures of the aforesaid. Synthetic sweeteners that can typically be used are sucralose, aspartame and saccharin. When a sweetener is used, its proportion is desirably from 0.1 to 5% wt. by weight, preferably from 0.5 to 4% wt., more preferably from 1 to 2% wt. related to the dry weight of the film or suspension.

c) Fillers

Additionally, a filler, for example, lactose, mannitol, calcium phosphate, calcium carbonate and mixtures thereof, may be present in the orodispersible film or the film forming suspension of the invention. Generally, a filler may be used when the plant extract is present in a low amount in the film or suspension.

d) Coloring Agents

Additionally, a coloring agent may be present in the film and in the suspension of the invention. Titanium oxide or iron oxide(s) may be used preferably.

EXAMPLES

Example 1

The film forming suspension was prepared by stirring 227.6 g of a water/ethanol solvent system (30% (v/v) ethanol) with 37.5 g of *hedera helix* dry leaf extract for 10 minutes at 200 rotations per minute (rpm). 20 g of hydroxypropyl methyl cellulose (Methocel E15LV) was added and stirred for another 2 minutes. Whilst stirring, 12.5 g of glycerol 85%, 11 g of microcrystalline cellulose, 5.5 g of maltodextrin, 1 g sucralose, 7.5 g raspberry flavor and 5 g titanium dioxide were slowly added. The stirring of the suspension was continued for 2 hours. The suspension was cast on a polyethylene terephthalate (PET) foil. The resulting laminate was dried at 50° C. for 15 minutes. After drying, the film was cut into squares of 2 cm$^2$, the foil was removed and the film packaged into sachets. The film met the content uniformity requirement according to Ph. Eur. 7.4 chapter 2.9.40. In addition, the pull-off properties of the obtained film were excellent and the film was elastic, not sticky and readily removed from the foil without any damages. The disintegration time was less than 20 seconds.

TABLE 1

| Example 1 | |
| --- | --- |
| *Hedera helix* leaf dry extract | 37.5 g |
| HPMC (Methocel E15LV) Mn 25.000 Da (g/mol), Mw 60000 Da (g/mol) | 20.0 g |
| Glycerol 85% | 12.5 g |
| Microcrystalline cellulose (Avicel PH 105) | 11.00 g |
| Maltodextrin | 5.5 g |
| Titanium oxide | 5.0 g |

TABLE 1-continued

| Example 1 | |
|---|---|
| Sucralose | 1.0 g |
| Raspberry flavor | 7.5 g |
| | 100.0 g |
| Ethanol | |
| Water | |

Ethanol and water are removed during the drying process

Comparative Example 2

The suspension and the film of example 2 were prepared according to the procedure of example 1. Metolose 60 SH-50 was used instead of Methocel E15LV.

TABLE 2

| Example 2 | |
|---|---|
| *Hedera helix* leaf dry extract | 37.5 g |
| HPMC (Metolose 60 SH-50) Mn 32.000 Da (g/mol), Mw 82.000 Da (g/mol) | 15.0 g |
| Glycerol 85% | 24.5 g |
| Microcrystalline cellulose (Avicel PH 105) | 9.50 g |
| Maltodextrin | 11.0 g |
| Sucralose | 2.0 |
| Raspberry flavour | 0.5 |
| | 100.0 g |
| Ethanol | |
| Water | |

Ethanol and water are removed during the drying process

The pull-off properties of the obtained film were insufficient as the film was not removable from the process liner.

Comparative Example 3

The suspension and the film of example 3 were prepared according to the procedure of example 1. A HPMC having a lower Mn and Mw with respect to the HPMC of the invention was used. The components and quantities thereof are reported in Table 3. The film obtained had poor mechanical strength and showed brittleness. It broke into pieces when removed from the process liner.

TABLE 3

| Example 3 | |
|---|---|
| *Hedera helix* leaf dry extract | 37.5 g |
| HPMC (Methocel E5LV) Mn 11.000 Da (g/mol), Mw 29.000 Da (g/mol) | 30.0 g |
| Glycerol 85% | 17.0 g |

TABLE 3-continued

| Example 3 | |
|---|---|
| Microcrystalline cellulose (Avicel PH 105) | 4.50 g |
| Maltodextrin | 11.0 g |
| | 100.0 g |
| Ethanol | |
| Water | |

Ethanol and water are removed during the drying process

Content Uniformity

Content uniformity was determined according to Ph. Eur. 7.4, chapter 2.9.40.

Pull-Off Adhesion Test

The pull-off-adhesion properties of the orodispersible film made according to example 1 was compared to the pull-off-adhesion properties of the orodispersible film of comparative examples 2 and 3. The test was performed by manually pulling off the orodispersible film from the support foil (as it is done by the health care personnel or the patient). Provided that the orodispersible film can be removed from the support foil without breaking into pieces and the weight of the orodispersible film removed from the support foil is within the range of +/−5% wt. compared to the calculated weight of the orodispersible film, the test is passed.

Disintegration Time Measurement

The disintegration time of the orodispersible film made according to example 1 was determined using the following test procedure: A Petri dish was filled with 4 ml of demineralized water having a temperature of 25° C. and was placed on a dark surface. The orodispersible film was taken out of the sachet with a pair of tweezers and was placed centered and horizontally onto the water surface. Time measurement starts when the film contacts the water. The disintegration of the film was observed visually. The disintegration time is the time at which the film starts disrupting in its central parts.

The invention claimed is:

1. An orodispersible film consisting essentially of:
   a) a plant extract selected from the group consisting of a *hedera helix* leaf extract, a *coptidis rhizoma* extract, a *primula veris* extract, a *primula elatior* extract, and a *thymus vulgaris* extract or a mixture thereof;
   b) hydroxypropyl methyl cellulose;
   c) microcrystalline cellulose;
   d) glycerol; and
   e) maltodextrin, wherein said orodispersible film rapidly disintegrates in the oral cavity of a patient in less than 20 seconds.

* * * * *